United States Patent
Dutta et al.

(10) Patent No.: US 7,611,613 B2
(45) Date of Patent: Nov. 3, 2009

(54) HIGH TEMPERATURE TOTAL $NO_x$ SENSOR

(75) Inventors: Prabir K. Dutta, Worthington, OH (US); Jiun-Chan Yang, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 764 days.

(21) Appl. No.: 11/195,508

(22) Filed: Aug. 2, 2005

(65) Prior Publication Data

US 2007/0029210 A1    Feb. 8, 2007

(51) Int. Cl.
*G01N 27/403*    (2006.01)
*G01N 27/407*    (2006.01)

(52) U.S. Cl. .................. 204/426; 204/412; 204/429; 205/781; 205/780.5

(58) Field of Classification Search ............... 204/426; 205/780.5
See application file for complete search history.

(56) References Cited

U.S. PATENT DOCUMENTS

| 5,403,452 | A | * | 4/1995 | Hielscher et al. ............ 205/781 |
| 5,667,652 | A | * | 9/1997 | Liu et al. .................... 204/412 |
| 6,764,591 | B1 | | 7/2004 | Dutta et al. |

OTHER PUBLICATIONS

Ono, M. et al., Solid State Ionics, 583, pp. 136-137, 2000.

Szabo, N.F. et al., "Microporous zeolite modified yttria stabilized zirconia &YSZ) sensors for nitric oxide (NO) determination in harsh environments", Sensors and Actuators B: Chemical, vol. 82, No. 2, Feb. 28, 2002, pp. 142-149.
Adler S.B., "Factors Governing Oxygen Reduction in Solid Oxide Fuel Cell Cathodes", Chem Rev. 104, pp. 4791-4843, 2004.
Bay, L. et al., "Dynamics of the YSZ-Pt interface", Solid State Ionics 93, pp. 201-206, 1997.
Bjorefors, F. et al., "Electrochemical Detection Based on Redox Cycling Using Interdigitated Microarray Electrodes at μL/min Flow Rates", Electroanalysis, 12, No. 4, pp. 255-261, 2000.
Brosha, E.L. et al., "Mixed potential sensors using lanthanum manganate and terbium yttrium zirconium oxide electrodes", Sensors and Actuators B 87, pp. 47-57, 2002.
Bruser, V. et al., "Nox-Determination with Galvanic Zirconia Solid Electrolyte Cells", Solid State Phenomena vols. 39-40, pp. 269-272, 1994.
Cabot, A. et al., "Mesoporous catalytic filters for semiconductor gas sensors", Thin Solid Films, 436, pp. 64-69, 2003.
Coillard, V. et al., "Nitrogen monoxide detection with a planar spinel coated amperometric sensor", Sensors and Actuators B 78, pp. 113-118, 2001.

(Continued)

*Primary Examiner*—Kaj K Olsen
*Assistant Examiner*—Kourtney R Salzman
(74) *Attorney, Agent, or Firm*—Calfee, Halter & Griswold LLP

(57) ABSTRACT

A total $NO_x$ sensor with minimal interferences from CO and $O_2$ includes a yttria-stabilized zirconia (YSZ) pellet and a Pt-loaded zeolite Y layer. Furthermore, three platinum wires are attached to the YSZ surface which operate as the working, counter and reference electrode. A potentiostat is connected to the electrodes to maintain a fixed potential between the reference and working electrode. The potentiostat then monitors the relationship between time and current through the counter electrode.

22 Claims, 7 Drawing Sheets

OTHER PUBLICATIONS

Docquier, N. et al., "Combusstion control and sensors: a review", Progress in Energy and Combusion Science 28, pp. 107-150, 2002.

Fleischer, M. et al., "Selective gas detection with high-temperature operated metal oxides using catalytic filters", Sensors and Actuators B 69, pp. 205-210, 2000.

Garzon, F.H. et al., "Solid-state mixed potential gas sensors: theory, experiments and challenges", Solid State Ionics, 136-137, pp. 633-638, 2000.

Gopel, W. et al., "Trends in the development of solid state amperometric and potentiometric high temperature sensors", Solid State Ionics, 136-137, pp. 519-531, 2000.

Gur, T.M. et al., "Importance of electrode/zirconia interface morphology in high-temperature solid electrolyte cells", J. of Applied Electrochemistry, 17, pp. 800-806, 1987.

Hua, L. et al, "Amperometric Detection of Carbohydrates by Capillary Electrophoresis with a Cuprous Oxide Modified Sol-Gel Carbon Composite Electrode", Electroanalysis, 12, No. 4, pp. 287-291, 2000.

Hubalek, J. et al., "Pt-loaded Al2O3 catalytic filters for screen-printed WO3 sensors highly selective to benzene", Sensors and Actuators B 101, pp. 277-283, 2004.

Hugon, O. et al., "Gas separation with a zeolite filter, application to the selectivity enhancement of chemical sensors", Sensors and Actuators B 67, pp. 235-243, 2000.

Kammer, K., "Electrochemical DeNOx in solid electrolyte cells-an overview", Applied Catalysis B: Environmental 58, pp. 33-39, 2005.

Kato, T. et al., "Influence of cell configuration on measuring interfacial impedances between a solid electrolyte and an electrode", Solid State Ionics 132, pp. 287-295, 2000.

Kitsukawa, S. et al., "The interference elimination for gas sensor by catalyst filters", Sensors and Actuators B 65, pp. 120-121, 2000.

Magori, E. et al., "Thick film device for the detection of NO and oxygen in exhaust gases", Sensors and Actuators B95, pp. 162-169, 2003.

Miura, N. et al., "Selective detection of NO by using an amperometric sensor based on stabilized zirconia and oxide electrode", Solid State Ionics, 117, pp. 283-290, 1999.

Miura, N. et al., "Progress in mixed-potential type devices based on solid electrolyte for sensing redox gases", Solid State Ionics, 136-137, pp. 533-542, 2000.

Miura, N. et al., "Stabilized zirconia-based sensor using oxide electrode for detection of NOx in high-temperature combustion-exhausts", Solid State Ionics, 86-88, pp. 1069-1073, 1996.

Miura, N. et al., "High-temperature potentiometric/amperometric NOx sensors combining stabilized zirconia with mixed-metal oxide electrode", Sensors and Actuators B 52, pp. 169-178, 1998.

Menil, F. et al., "Critical review of nitrogen monoxide sensors for exhause gases of lean burn engines", Sensors and Actuators B 67, pp. 1-23, 2000.

Ono, M. et al., "Amperometric sensor based on NASICON and NO oxidation catalysts for detection of total NOx in atmospheric environment", Solid State Ionics, 136-137, pp. 583-588, 2000.

Ono, T. et al., "Performance of the NOx sensor based on mixed potential for automobiles in exhaust gases", JSAE Review, 22, pp. 49-55, 2001.

Reinhardt, G. et al., "Sensing small molecules with amperometric sensors", Solid State Ionics, 150, pp. 79-92, 2002.

Schwandt, C. et al., "Variation of the oxygen exhange rate of zirconia-based electrodes by electrochemical pretreatment", Solid State Ionics, 112, pp. 229-236, 1998.

Skelton, D.C. et al., "A surface-science-based model for the selectivity of platinum-gold alloy electrodes in zirconia-based NOx sensors", Sensors and Actuators B 96, pp. 46-52, 2003.

Sridhar, S. et al., "Transient and Permanent Effects of Direct Current on Oxygen Transfer across YSZ-Electrode Interfaces", J. Electrochem. Soc. vol. 144, No. 7, pp. 2479-2485, Jul. 1997.

Szabo, N.F. et al., "Strategies for total NOx measurement with minimal CO interference utilizing a microporous seolitic catalytic filter", Sensors and Actuators B 88, pp. 168-177, 2003.

Trimboli, J. et al., "Oxidation chemistry and electrical activity of Pt on titania: development of a novel zeolite-filter hydrocarbon sensor", Sensors and Actuators B 102, pp. 132-141, 2004.

Walsh, K.J. et al., "Nitric oxide reduction using platinum electrodes on yttria-stabilized zirconia", Solid State Ionics, 93, pp. 17-31, 1997.

Wang, J. et al., "Enhanced Stability of Glassy Carbon Detectors following a Simple Electrochemical Pretreatment", Anal. Chem., 58, pp. 1787-1790, 1986.

Warburton, P.R. et al., "Amperometric Gas Sensor Response Times", Anal. Chem, 70, pp. 998-1006, 1998.

Schmidt-Zhang, P. et al., "A novel thick film sensor for simultaneous O2 and NO monitoring in exhaust gases", Sensors and Actuators, B 70, pp. 25-29, 2000.

de Graaf, J. et al., "Preparation of Highly Dispersed Pt Particles in Zeolite Y with a Narrow Particle Size Distribution: Characterization by Hydrogen Chemisorption, TEM, EXAFS Spectroscopy, and Particle Modeling", J. of Catalysis, 203, pp. 307-321, 2001.

Fritz, A. et al., "The current state of research on automotive lean NOx catalysis", Applied Catalysis B: Environmental 13, pp. 1-25, 1997.

Lu, G. et al., "High-temperature sensors for NO and NO2 based on stabilized zirconia and spinel-type oxide electrodes", J. Mater. Chem. 7 (8), pp. 1445-1449, 1997.

Yang, J.C. et al. "High temperature amperometric total NOx sensors with platinum-loaded zeolite Y electrodes", Science Direct, Sensors and Actuators B 123, pp. 929-936, 2007, available on-line Dec. 4, 2006.

\* cited by examiner

HIGH TEMPERATURE TOTAL $NO_x$ SENSOR

BACKGROUND

There is a continuing need for high temperature $NO_x$ sensors for controlling combustion environments to meet government regulations and minimize negative effects of $NO_x$ on ecosystems and health. The two main types of electrochemical sensors that have been tested for $NO_x$ are semiconductor sensors and potentiometric sensors. One of the main drawbacks of these sensors that has hindered their development is the lack of selectivity between the two main $NO_x$ components of interest, NO and $NO_2$.

In combustion environments NO is often the dominant $NO_x$ species with $NO_2$ being present to a lesser amount. However, the majority of sensors cannot distinguish between the two species giving a signal response to both NO and $NO_2$. Most solid-state sensors are dedicated to detecting NO only as NO is the major component of $NO_x$ at high temperatures. However, depending on the temperature and oxygen content $NO_2$ can also be present and sensors that measure total $NO_x$ (NO+$NO_2$) are required.

With electrochemical sensors, $NO_2$ generally tends to get reduced and NO tends to be oxidized to generate opposite electrical signals. CO is a major component in a typical combustion exhaust and tends to readily oxidize to $CO_2$. As a result, the electrical signal generated by the oxidation of CO can obscure the $NO_x$ signal. Interference due to changes in $O_2$ concentration is also considered to be a major issue.

There have been attempts to solve this problem by using multi-chamber designs that measure total $NO_x$ and minimize interference due to CO and $O_2$. However, these multi-chamber designs are very complicated and difficult to manufacture.

SUMMARY

A total $NO_x$ sensor is described which is capable of detecting the total $NO_x$ that is present in a gas environment having fluctuating CO and oxygen. This new design is compact, does not require complicated multi-chamber structures or external air references, is simple and inexpensive to fabricate and manufacture, which enables more flexibility and placement of the sensor inside a combustion device.

The $NO_x$ sensor includes a yttria-stabilized zirconia (YSZ) pellet and a Pt-loaded zeolite Y layer. Furthermore, three platinum wires are attached to the YSZ surface which operate as the working, counter and reference electrode. A potentiostat is connected to the electrodes to maintain a fixed potential between the reference and working electrode. The potentiostat then monitors the current through the counter electrode in the presence of sensing gas.

Numerous other advantages and features of the present invention will become readily apparent from the following detailed description of the invention and the embodiments thereof, from the claims and from the accompanying drawings.

BRIEF DESCRIPTION OF THE DRAWINGS

The invention as well as embodiments and advantages thereof are described below in greater detail, by way of example, with reference to the drawings in which.

DETAILED DESCRIPTION

Figure 1:
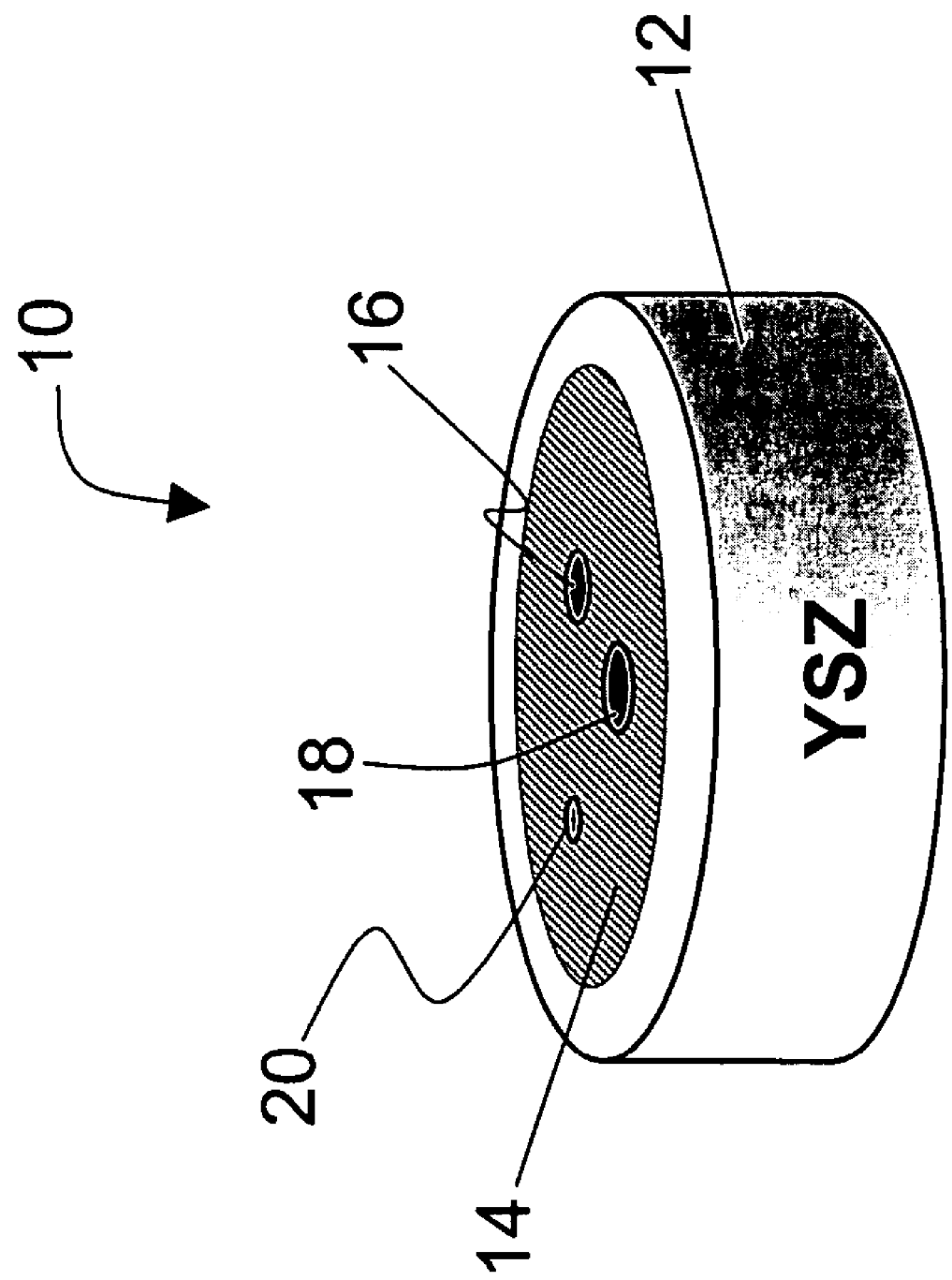
FIG. 1 is a perspective view of the $NO_x$ sensor in accordance with an embodiment of the present invention.

While this invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

Referring to FIG. 1, one embodiment of a $NO_x$ sensor 10 is illustrated. The $NO_x$ sensor 10 comprises a yttria-stabilized zirconia (YSZ) pellet 12 and a catalytic filter 14. The catalytic filter of FIG. 1 is a Pt-loaded zeolite Y layer, however the catalytic filter 14 may include other materials such as Pt-loaded silica or Pt-loaded alumina. Furthermore, the Pt loading ranges generally from 0.1 to 10 wt %.

There are three electrodes attached to a surface of the YSZ pellet 12. The three electrodes include a working electrode 16, a counter electrode 18 and a reference electrode 20. In the embodiment of FIG. 1, each electrode includes a platinum wire that is attached to the surface of the YSZ pellet 12 using a small amount of Pt ink. However, other materials may be used to form the electrodes, such as $WO_3$, NiO and other noble metals and metal oxides. Similarly, other materials and methods may be used to attach the electrodes to the surface of the YSZ pellet 12. The platinum wires may be used, in conjunction with a potentiostat, for example, to manage or monitor the electrical properties of the sensor 10.

The sensor 10 also ideally operates at high temperatures. For example, the sensor 10 can operate most effectively at temperatures of 300° C.-700° C. and more preferably 450° C.-600° C.

Figure 2:
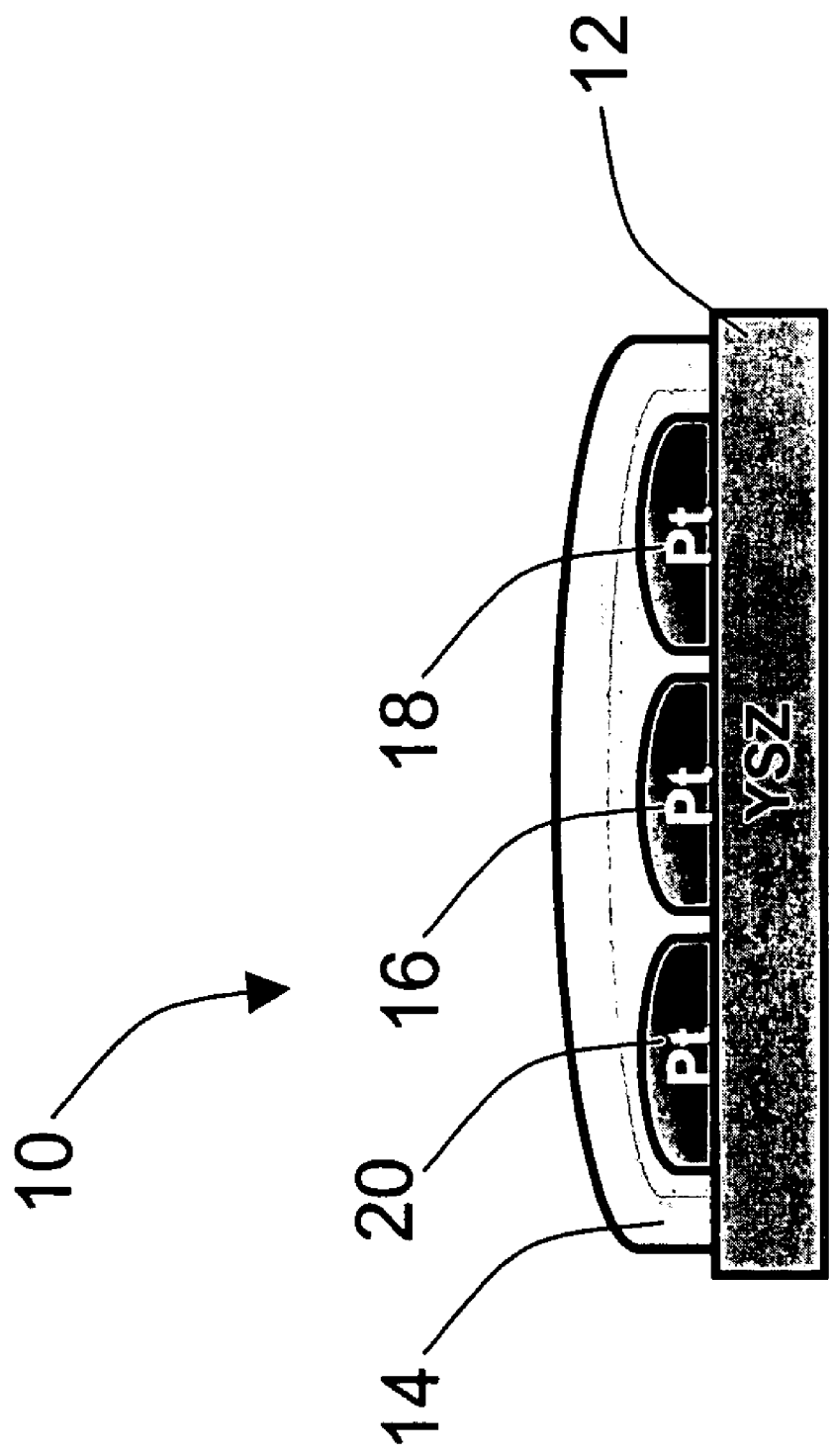
FIG. 2 is a schematic cross-sectional drawing of the sensor of FIG. 1.

Referring now to FIG. 2, a schematic cross-sectional view of the sensor 10 is shown. To make the sensor 10 of FIG. 2, Pt-loaded zeolite Y was synthesized from commercial Na-exchanged zeolite Y (NaY). Specifically, 1.0 g of NaY powder was dried at 100° C. for four hours and them was mixed with 5 mM [Pt($NH_3$)$_4$]$Cl_2$ solution. The mixture was stirred for 24 hours at room temperature for ion exchange. The mixture was then centrifuged and washed with distilled water several times to remove unwanted ions and dried at 70° C. for three hours. After calcination at 300° C. for 2 hours, the calcined zeolite was exposed to a flowing gas mixture of 5% $H_2$ balance $N_2$ to reduce $Pt^{2+}$ to metal Pt.

The three electrodes were made by attaching a cleaned Pt wire to the YSZ pellet 12 with a very small amount of Pt ink. The Pt ink was cured at 1200° C. for two hours to secure the bonding between the electrodes and the YSZ pellet 12. About 10 mg of PtY was mixed with α-terpineol to form a paste and applied over the three Pt electrodes. After curing in air at 650° C. for 2 hours, the thickness of the PtY layer 14 is approximately 50 μm.

Figure 3:
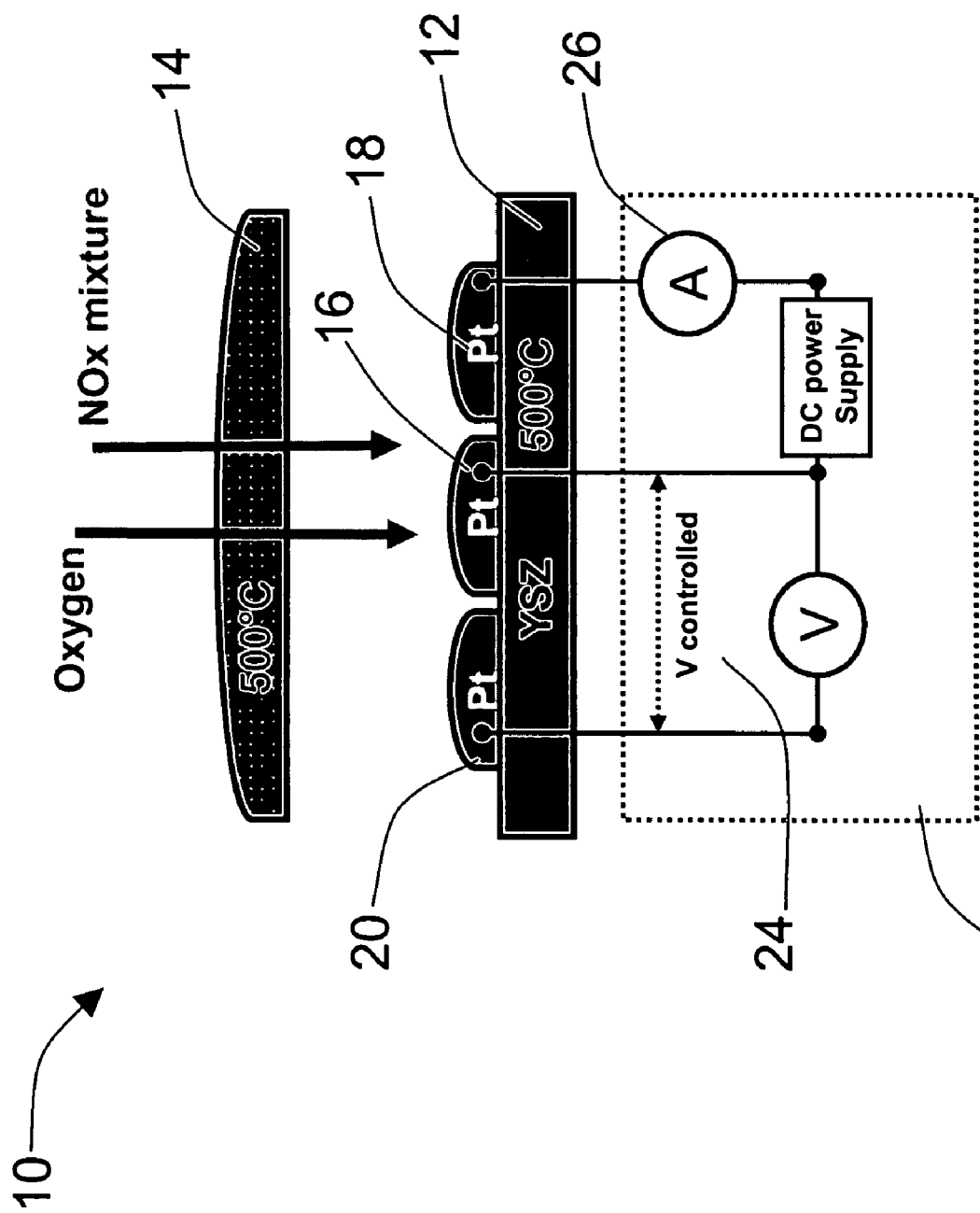
FIG. 3 is a schematic cross-sectional drawings of a $NO_x$ sensor in accordance with another embodiment of the present invention.

The electrodes of the sensor 10 are then connected to a potentiostat 22 as shown in FIG. 3. Specifically, the potentiostat 22 maintains a constant voltage 24 potential between the reference electrode 20 and working electrode 16, while measuring the current 26 between the working electrode 16 and the reference electrode 18.

It was determined through experiments discussed below that there is a linear relationship between $NO_x$ concentration and the current flowing through the counter electrode 18 as measured by the potentiostat 22 when an potential (of about 50-100 mV) is held constant between the working electrode 16 and the reference electrode 20. It was further determined that NO and $NO_2$ produce almost the same magnitude of signal because they have been equilibrated when diffusing through the PtY layer 14. This is true if the PtY layer 14 is attached to the YSZ pellet 12 as shown in FIG. 1 of if the PtY layer 14 is separate from the YSZ pellet 12 as shown in FIG. 3. Furthermore, the PtY layer 14 and the YSZ pellet can be kept at the same temperature because the potential is used to slightly perturb $NO_x$ equilibrium that results from $NO_x$ passing through the PtY layer 14. This provides a great advantage to other types of sensors which require the PtY filter 14 to be at a different temperature than the YSZ pellet 12 since only one heating source is needed instead of two.

Figure 4:
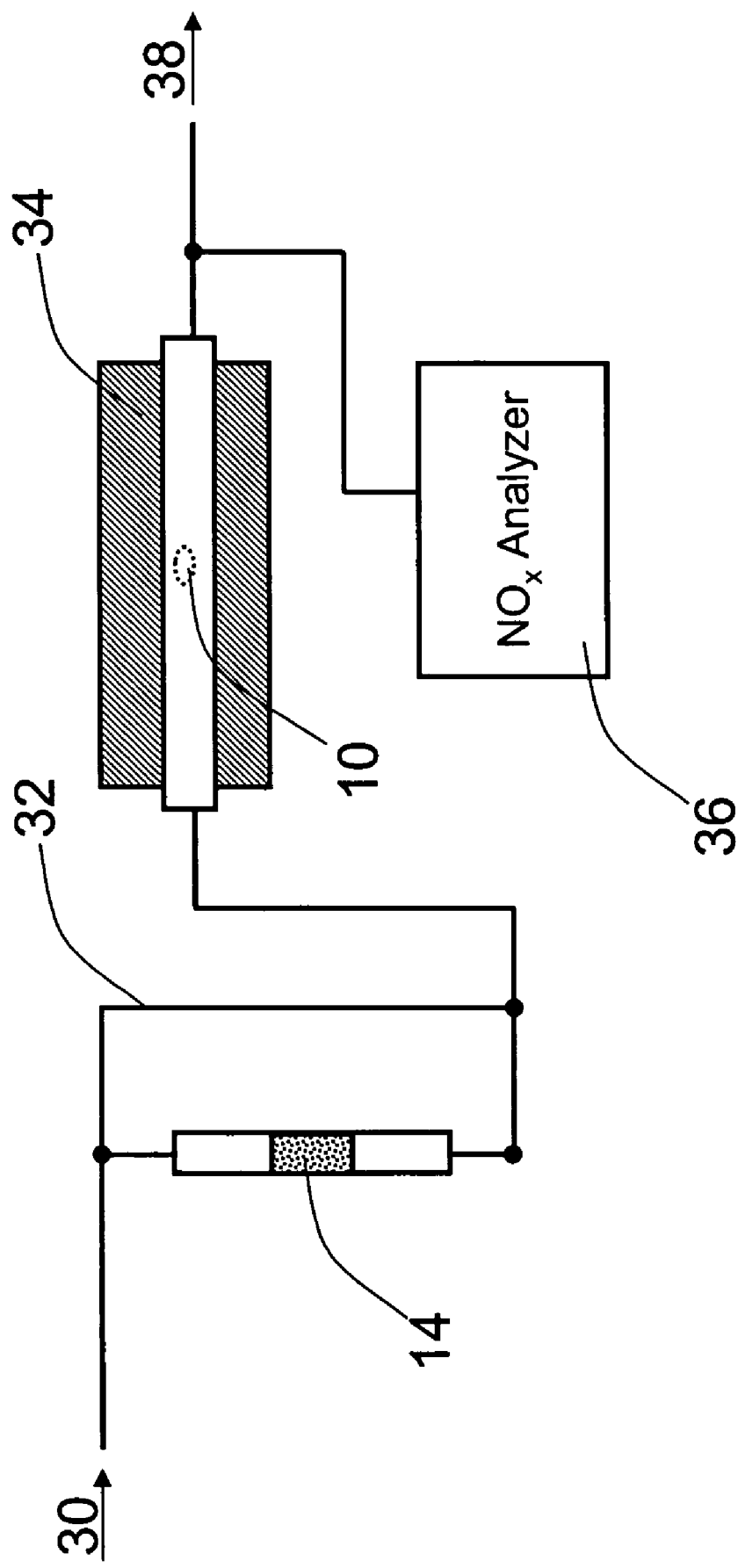
FIG. 4 is a diagram of the experimental set-up used in conjunction with the present invention.

To test the sensor 10, a series of experiments were conducted having the set-up shown in FIG. 4. Four certified $NO_x$ cylinders (30 ppm NO, 30 ppm NO2, 2000 ppm NO, 2000 ppm $NO_2$) were used as $NO_x$ input sources 30. A PtY filter 14 having 40 mg PtY was disposed on a support-frit within a vertically placed quartz tube. The filter 14 was heated to 500° C. A filter bypass 32 was used to allow gases to bypass the filter 14 when desired. The sensor 10 was disposed within a quartz tube inside a tube furnace 34 (Lindberg Blue, TF55035A) and was heated to 500° C. A chemiluminescent $NO_x$ analyzer 36 (Eco-Physics CLD 70S) was connected to the outlet 38 of the tube furnace 34 to measure the $NO_x$ concentration output from the furnace 34. The current-voltage polarization curve (I-V curve), chronoamperometric measurements, and electrochemical impedance spectra were recorded by a potentiostat (Gamry DC105). The potential difference between the electrodes was monitored by a Hewlett-Packard data acquisition system (HP, 34970A) with 10 GΩ internal impedance.

The embodiments shown in FIGS. 1 and 3 of the sensor 10 were tested. When the embodiment of FIG. 1 (i.e. filter 14 disposed over electrodes on YSZ pellet 12) was tested, the filter bypass 32 was used so that the gas mixture did not flow through the filter 14 before reaching the tested sensor 10 in the furnace 34. However, then the embodiment of FIG. 3 (i.e. filter 14 separate from electrodes and YSZ pellet 12) was tested, the filter bypass 32 was closed and filter 14 was used as the PtY layer 14 and the sensor 10 disposed in the furnace 34 did not contain a PtY layer 14 over the electrodes and YSZ pellet 12.

As shown in FIG. 4, the $NO_x$ gas mixture from a computer controlled mass flow controller (MFC) introduced the $NO_x$ gas into the test system. The flow rate was controlled between 100 ml/min and 300 ml/min. The potentiostat then applied an potential of an 80 mV between the reference electrode 20 and the working electrode 16, and subsequently recorded the current as a function of time as the $NO_x$ gas pass through the furnace 34. The chemiluminescent $NO_x$ analyzer 36 then recorded the actual $NO_x$ concentration. The results are shown in FIGS. 5a and 5b.

Figure 5A:
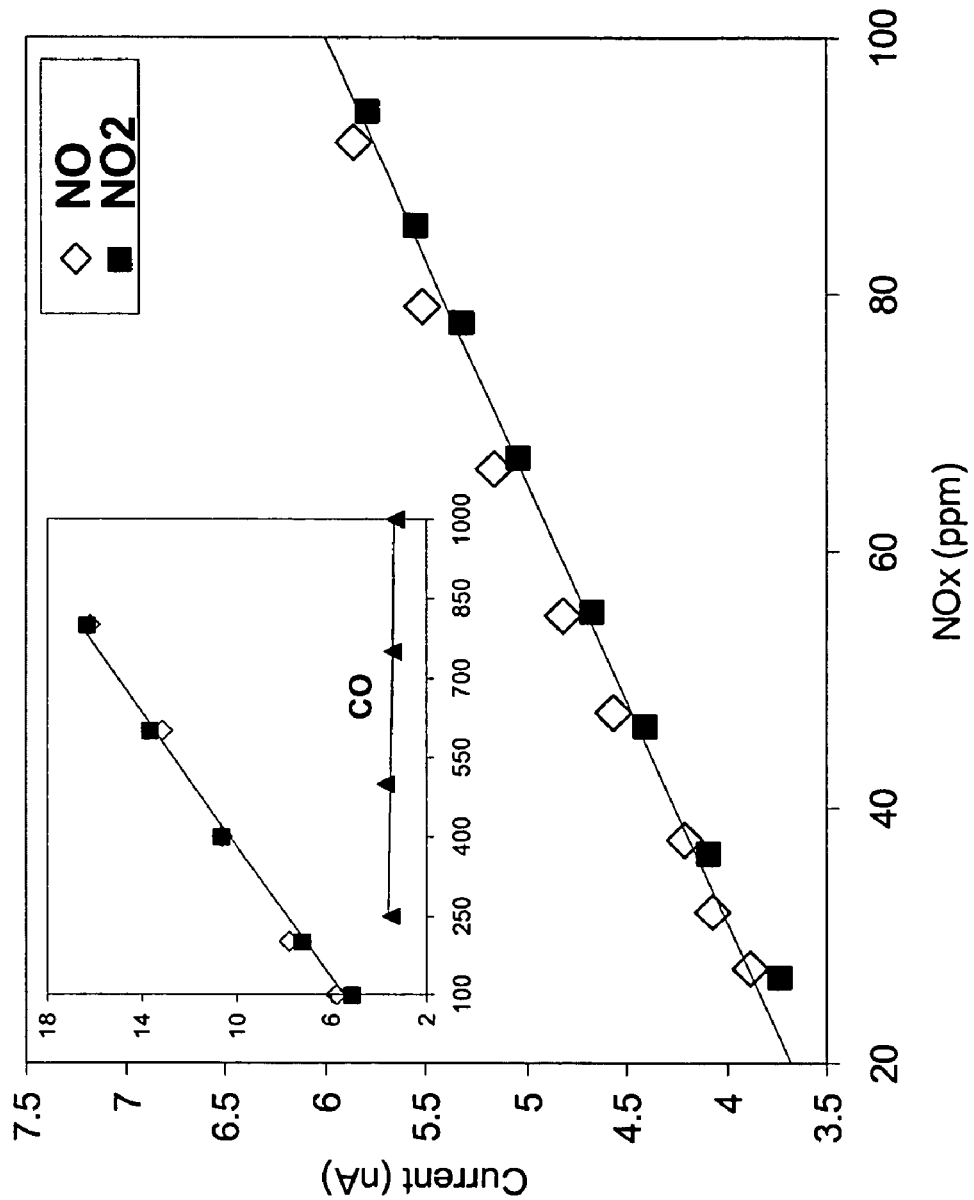
FIG. 5a is a graph showing the relationship between $NO_x$ concentration and current.
Figure 5B:
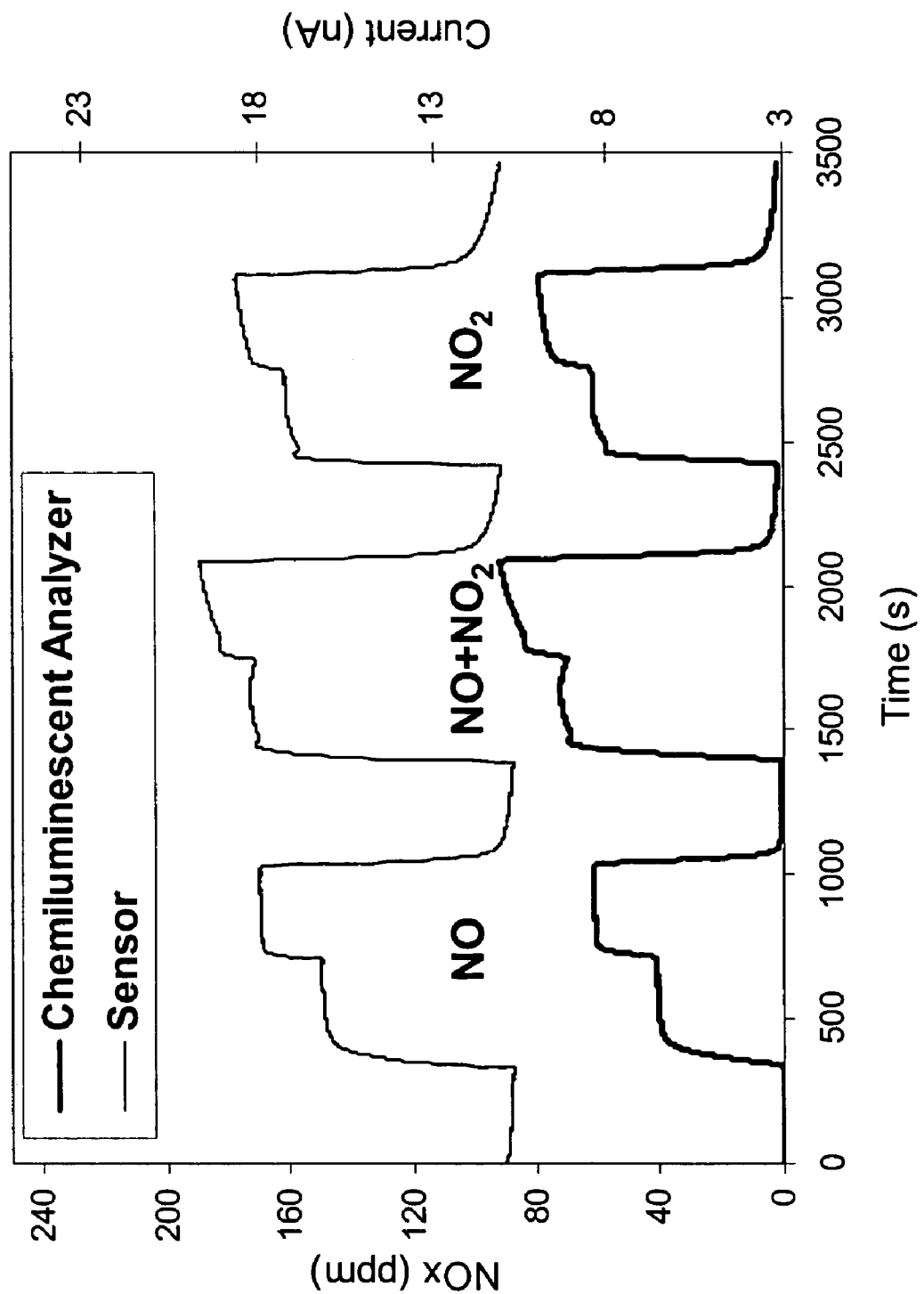
FIG. 5b is a graph showing the sensing performance of the $NO_x$ sensor compared to the sensing performance of a commercial chemiluminescent $NO_x$ analyzer.

As shown in FIG. 5a, the relationship between the $NO_x$ concentration and current is linear. As shown in FIG. 5b, the sensing performance of the sensor 10 tracks the actual measured $NO_x$ concentration as measured by the chemiluminescent $NO_x$ analyzer 36. The actual $NO_x$ concentration can then be obtained by multiplying the measured current by a proper calibration constant. Thus, the sensor 10 accurately measures the total $NO_x$ concentration during very practical conditions for modern combustion units such as lean burn engines.

Figure 6:
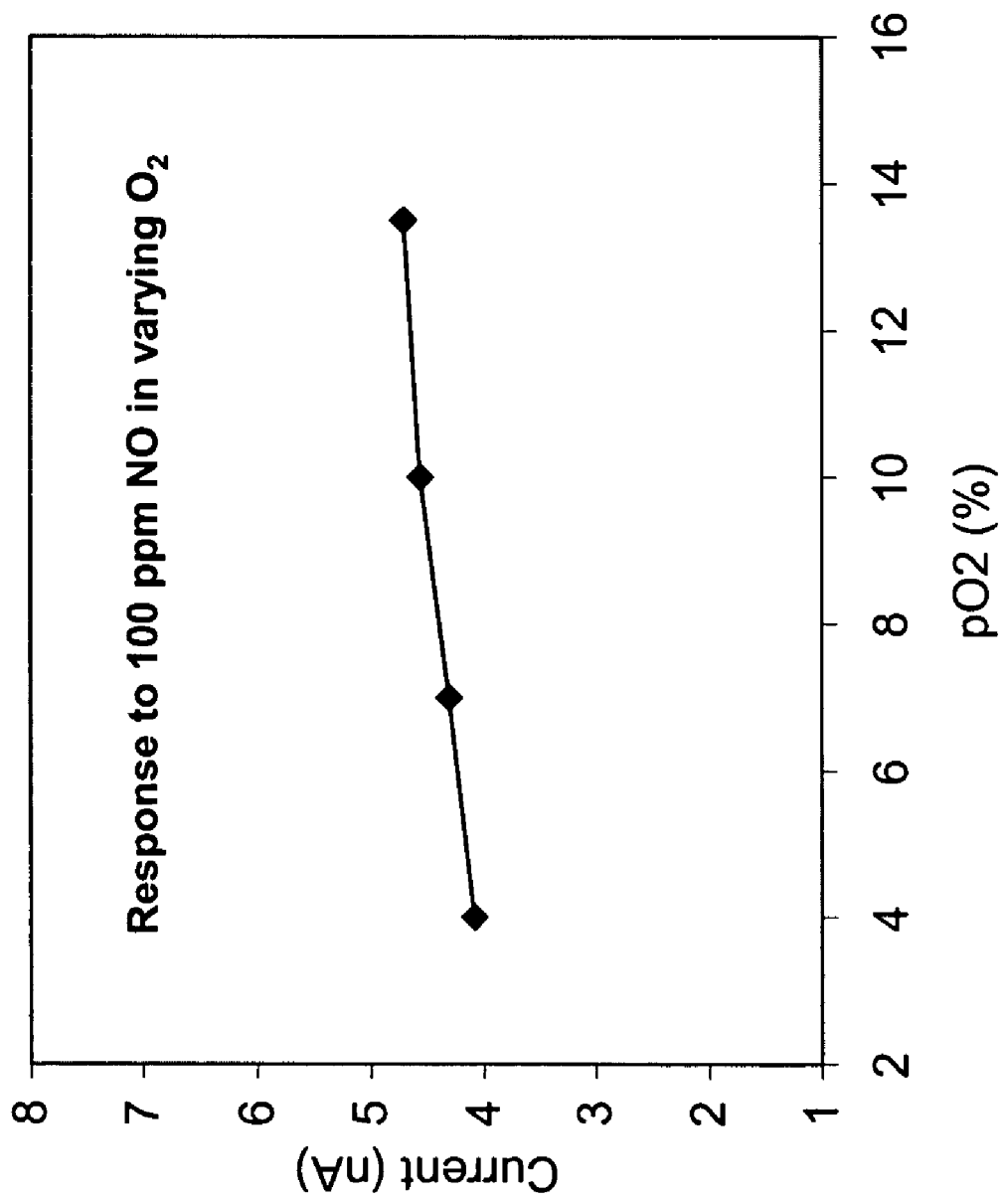
FIG. 6 is a graph showing the variances of in the sensor when exposed to varying levels of $O_2$ interference.

Furthermore, CO interference is a major problem for current $NO_x$ sensors. The insert in FIG. 5a shows that the sensor 10 is nearly insensitive to the presence of CO. This is because CO is oxidized to $CO_2$ which cannot be further oxidized on the working electrode when passing through the PtY layer 14. FIG. 6 shows the minimal variation of the current for 100 ppm NO in the presence of varying backgrounds of $O_2$. As a result, the sensor 10 is an effective high temperature $NO_x$ sensor even in the presence of CO and $O_2$. Therefore, the present sensor 10 is effective for use in the gas flow of modern combustion engines such as automobiles. In such systems, the $NO_x$ sensor 10 can be used to monitor $NO_x$ for checking emissions of the exhaust as well as to optimize any $NO_x$ after-treatment system.

The above description of some of the embodiments of the present invention has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. An amperometric sensor for simultaneously measuring NO and $NO_2$ contained in a gas flowing through a conduit comprising:
   a YSZ pellet having a first surface, to be contacted by the gas during operation of the sensor;
   a reference electrode electrically connected to and disposed on the first surface;
   a counter electrode electrically connected to and disposed on the first surface;
   a working electrode electrically connected to and disposed on the first surface;
   a catalytic filter disposed upstream of the first surface; and
   an electrical device operable to apply a constant positive or negative voltage between the reference electrode and the working electrode while the gas contacts the first surface, the electrical device operable to measure current flowing through the counter electrode while the gas contacts the first surface,
   wherein operation of the sensor does not require a temperature difference between the catalytic filter and the YSZ pellet.

2. The sensor of claim 1 wherein the catalytic filter and said the YSZ pellet are maintained within the same temperature range.

3. The sensor of claim 2 wherein the temperature range is between 300-700° C.

4. The sensor of claim 2 wherein the temperature range is between 450-600° C.

5. The sensor of claim 1 wherein the catalytic filter is disposed over the electrodes and on the first surface.

6. The sensor of claim 1 wherein the catalytic filter is a Pt-loaded zeolite Y filter.

7. The sensor of claim 1 wherein the catalytic filter is a Pt-loaded silica Y filter.

8. The sensor of claim 1 wherein the catalytic filter is a Pt-loaded alumina filter.

9. The sensor of claim 1 wherein the catalytic filter is Pt-loaded in a range of 0.1 to 10 wt %.

10. The sensor of claim 1 wherein the electrical device is a potentiostat.

11. An automobile comprising:
a combustion engine having an exhaust conduit;
an amperometric sensor for simultaneously measuring NO and $NO_2$ contained in a gas flowing though the exhaust conduit comprising:
a YSZ pellet having a first surface to be contacted by the gas during operation of the sensor;
a reference electrode electrically connected to and disposed on the first surface;
a counter electrode electrically connected to and disposed on the first surface;
a working electrode electrically connected to and disposed on the first surface;
a catalytic filter disposed upstream of the first surface; and
an electrical device operable to apply a constant positive or negative voltage between the reference electrode and the working electrode while the gas contacts the first surface, the electrical device operable to measure current flowing through the counter electrode while the gas contacts the first surface,
wherein operation of the sensor does not require a temperature difference between the catalytic filter and the YSZ pellet.

12. The automobile of claim 11 wherein the catalytic filter and the YSZ pellet are maintained within the same temperature range.

13. The automobile of claim 12 wherein the temperature range is between 300-700° C.

14. The automobile of claim 13 wherein the temperature range is between 450-600° C.

15. The automobile of claim 11 wherein the catalytic filter is disposed over the electrodes and on the first surface.

16. The automobile of claim 11 wherein the catalytic filter is a Pt-loaded zeolite Y filter.

17. The automobile of claim 11 wherein the electrical device is a potentiostat.

18. The automobile of claim 11 wherein the electrical device includes feedback to control air/fuel mixture for optimal combustion, minimizing emissions and monitoring NO and $NO_2$ after treatment systems.

19. A method of simultaneously measuring NO and $NO_2$ contained in a gas flowing through a conduit comprising the steps of:
conducting the gas through an amperometric sensor, the sensor comprising:
a YSZ pellet having a first surface to be contacted by the gas during operation of the sensor;
a reference electrode electrically connected to and disposed on the first surface;
a counter electrode electrically connected to and disposed on the first surface;
a working electrode electrically connected to and disposed on the first surface;
a Pt-loaded zeolite Y filter disposed upstream of the first surface; and
an electrical device operable to apply a constant positive or negative voltage between the reference electrode and the working electrode while the gas contacts the first surface, the electrical device operable to measure current flowing through the counter electrode while the gas contacts the first surface, wherein operation of the sensor does not require a temperature difference between the catalytic filter and the YSZ pellet;
measuring the current while the gas contacts the sensor; and
multiplying the measured current by a calibration constant to measure the amount of NO and $NO_2$.

20. The method of claim 19 wherein said Pt-loaded zeolite Y filter and said YSZ pellet are maintained within the same temperature range.

21. The method of claim 19 wherein the Pt-loaded zeolite Y filter is disposed over the electrodes and on said first surface.

22. The method of claim 20 wherein the temperature range is between 300-700° C.

* * * * *

UNITED STATES PATENT AND TRADEMARK OFFICE
CERTIFICATE OF CORRECTION

| | |
|---|---|
| PATENT NO. | : 7,611,613 B2 |
| APPLICATION NO. | : 11/195508 |
| DATED | : November 3, 2009 |
| INVENTOR(S) | : Prabir K. Dutta et al. |

It is certified that error appears in the above-identified patent and that said Letters Patent is hereby corrected as shown below:

On the Title Page, Item (*) Notice, delete "764 days" insert --1128 days--

Column 1, between lines 1 and 2, please insert the following new paragraph:

--This invention was made with government support under DE-FC26-03NT41615 awarded by the Department of Energy. The government has certain rights in the invention.--

Signed and Sealed this

Seventh Day of September, 2010

David J. Kappos
*Director of the United States Patent and Trademark Office*